US00PP37770P2

(12) United States Plant Patent
Korlipara

(10) Patent No.: US PP37,770 P2
(45) Date of Patent: Oct. 13, 2026

(54) ***GEUM COCCINEUM* PLANT NAMED 'FIESTA'**

(50) Latin Name: *Geum coccineum*
Varietal Denomination: Fiesta

(71) Applicant: Terra Nova Nurseries, Inc., Canby, OR (US)

(72) Inventor: Harini Korlipara, Tualatin, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 19/567,767

(22) Filed: Mar. 16, 2026

(51) Int. Cl.
*A01H 5/02* (2018.01)
*A01H 6/74* (2018.01)

(52) U.S. Cl.
USPC ..... Plt./263.1

(58) Field of Classification Search
USPC ..... Plt./263.1
See application file for complete search history.

(56) References Cited

U.S. PATENT DOCUMENTS

PP31,209 P2 * 12/2019 Korlipara ..... A01H 5/02
Plt./263.1

* cited by examiner

*Primary Examiner* — Karen M Redden
(74) *Attorney, Agent, or Firm* — Klarquist Sparkman, LLP

(57) ABSTRACT

A new and distinct *Geum coccineum* plant named 'Fiesta' is disclosed, characterized by its multicolor picotee flowers in bright yellow, orange and red, fall rebloom, and clean summer foliage.

2 Drawing Sheets

Latin name of the genus and species of the plant claimed: *Geum coccineum.*

Variety denomination: 'FIESTA'.

BACKGROUND

The present application relates to a new and distinct variety of *Geum coccineum* named 'Fiesta'. The cultivar is also known by its tradename, TEMPO™ 'Fiesta'. *Geum coccineum* is a species of flowering plant in the Rosaceae family. It is typically a clump-forming perennial that is grown ornamentally. *Geum coccineum* 'Fiesta' originated as part of a planned breeding program to produce *Geum* with upright flowers, unique colors, and good rebloom.

SUMMARY

The new variety 'Fiesta' is distinguished from other *Geum coccineum* varieties due to the following unique combination of characteristics:

1. Multicolored picotee flower color in bright orange, yellow, and red
2. Fall rebloom
3. Clean summer foliage The seed donor (female) parent is 'G20422', an unpatented and undescribed proprietary seedling. The pollen donor (male) parent is an unknown, unpatented, unnumbered, unnamed, and now extinct proprietary seedling.

Compared to TEMPO™ 'Yellow' (unpatented), which has all yellow petals, the multicolored petals of 'Fiesta' are bright orange, yellow, and red. In addition, TEMPO™ 'Yellow' grows to an overall height of 51 cm whereas 'Fiesta' typically has a maximum height of 37 cm.

As compared to TEMPO™ 'Orange' (unpatented), which has all orange petals, the multicolored petals of 'Fiesta' are bright orange, yellow, and red. 'Fiesta' is also shorter in height as compared to TEMPO™ 'Orange' (unpatented), which grows to an overall height of 38.1 cm.

The new cultivar has been reproduced only by asexual propagation (tip cuttings and tissue culture using growing tips). Each of the progeny exhibit identical characteristics to the original plant. Asexual propagation by cuttings and tissue culture were performed using standard micropropagation techniques with terminal and lateral shoots in Canby, Oregon.

Asexual reproduction of 'Fiesta' shows that the characteristics described herein come true to form, are firmly fixed, and are established and transmitted through succeeding propagations.

BRIEF DESCRIPTION OF THE DRAWING(S)

Figure 1:
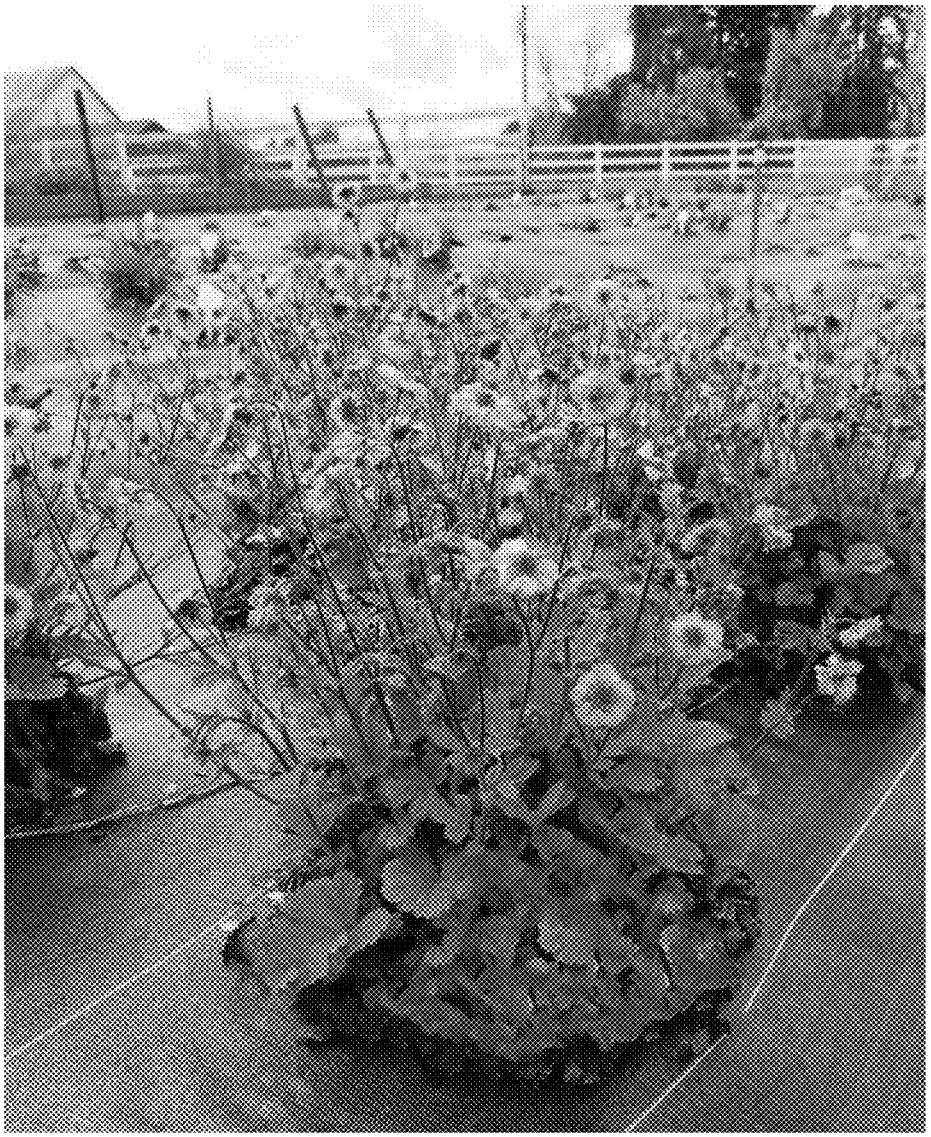
FIG. 1 shows a 17-month-old specimen grown outdoors in full sun in Canby, Oregon. The photograph was taken under natural outdoor light in May 2024.
Figure 2:
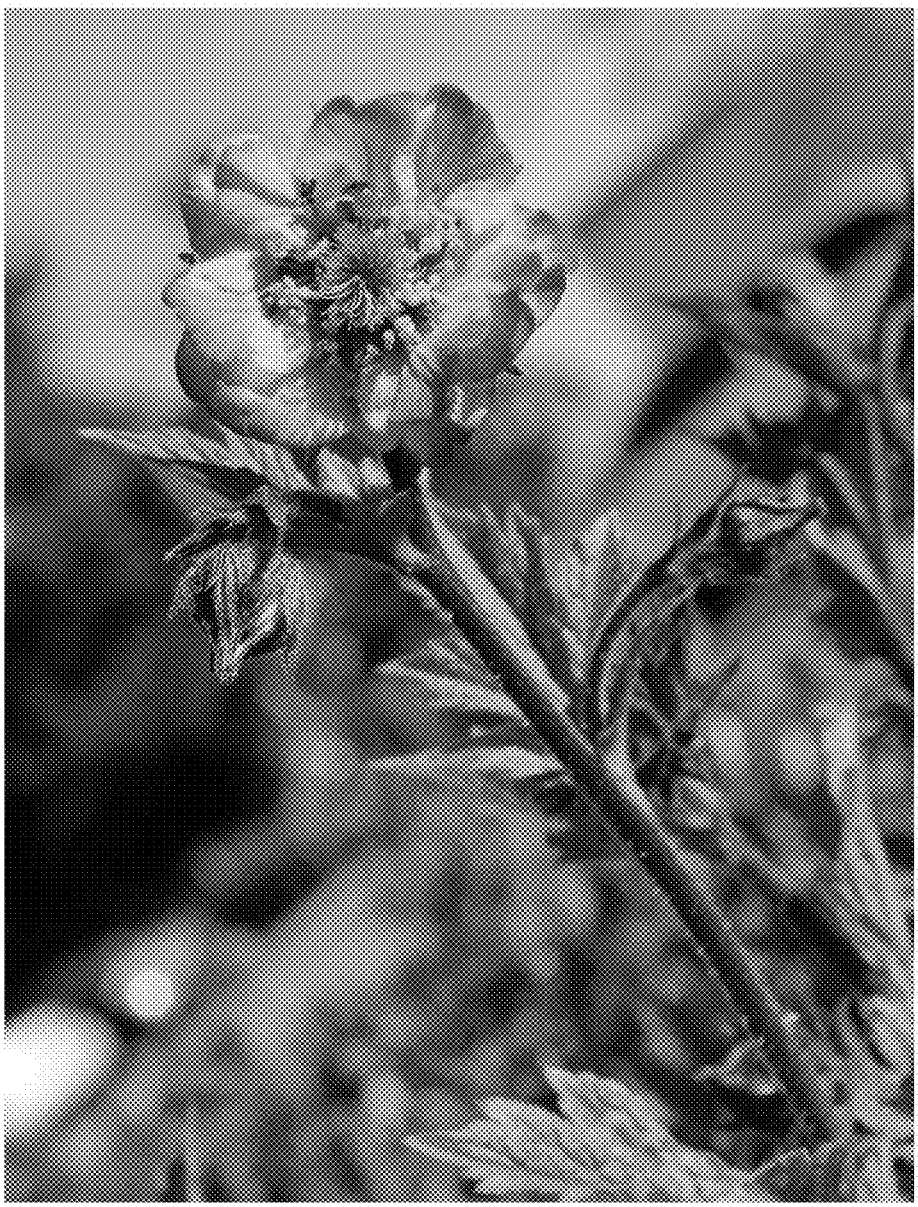
FIG. 2 shows a close-up of a bloom on a 28-month-old specimen grown outdoors in full sun in Canby, Oregon. The photograph was taken under natural outdoor light in April 2025.

The color photographs show typical specimens of the new variety and depict the color as nearly true as is reasonably possible to make the same in a color illustration of this character. It should be noted that colors may vary, for example, due to lighting conditions at the time a photograph is taken. Therefore, color characteristics of this new variety should be determined with reference to the observations described herein, rather than from the photographs alone.

DETAILED DESCRIPTION

The following detailed description of 'Fiesta' is based on observations taken in the month of April of a 28-month-old asexually reproduced progeny that was field grown in full sun in Canby, Oregon. Canby is Zone 8 on the USDA Hardiness map. Temperatures range from a high of 95° F. in August to an average low of 32° F. in January. Normal rainfall in Canby is 42.8 inches per year.

The new cultivar has not been evaluated under all possible environmental conditions and certain characteristics may change with changing environmental conditions (such as photoperiod, temperature, moisture, soil conditions, nutrient availability, or other factors). The phenotype may change with variations in environment without a change in the genotype of the plant.

Color descriptions and other terminology are used in accordance with their ordinary dictionary descriptions, unless the context clearly indicates otherwise. Color descriptions used herein are made with reference to *The Royal Horticultural Society Colour Chart,* 5$^{th}$ edition, 2007.

Parentage:

*Female parent.*—'G20422'.

*Male parent.*—Unknown.

Plant:

*Type.*—Herbaceous perennial.

*Form.*—Mound with 20 to 40 crowns.

*Plant height.*—26 cm to top of foliage, 37 cm to top of flowers.

*Plant width.*—44 cm.

*Persistence.*—Dies down to the crown in winter.

*Vigor.*—Excellent.

*Hardiness.*—USDA Zones 5-9.

Leaves:

*Type.*—Simple, rosulate.

*Arrangement.*—Basal rosette.

*Number of leaves.*—About 210 per plant.

*Texture.*—Pubescent on both sides.

*Color.*—Top: RHS 147A, including veins. Bottom: RHS 147B, including veins.

*Venation.*—Pinnate and impressed.

*Rosulate leaves.*—Lyrate-pinnate, foliate, with leaflets in pairs in declining size below the terminal leaflet (smallest to 8 mm wide, 7 mm long); terminal leaflet largest, rhomboid, grows to 5.6 cm long and 8 cm wide, 3-5 lobed, truncate base, margins irregularly serrate, tip obtuse to notched to acute; top lateral leaflets, 4.2 cm wide, 3.2 cm long, irregularly obovate, margins irregularly serrate, opposite, tips acute to obtuse, bases cuneate, sessile.

*Petiole.*—Color: RHS 145A, tinged at the base with RHS 187C. Petiole Base: Clasping. Size: Grows to 10 cm long and 3 mm wide (8 mm wide at flared base). Texture: Pubescent.

Stem: None.

Flowers:

*Inflorescence.*—2 to 4 cymes from each crown with 1 to 6 flowers per cyme.

*Attitude.*—Upright to semi-upright.

*Peduncle.*—Grows to 21 cm tall and 3.5 mm wide.

*Peduncle texture.*—Pubescent.

*Peduncle color.*—RHS 144B where shaded and RHS N77A where exposed to sun.

*Peduncle leaves.*—Lyrate, petiolate with petioles to 6 mm long, blade grows to 3.5 cm long and 2.2 cm wide, 3-lobed, serrate, tips attenuate, base cuneate, pubescent on both sides.

*Peduncle strength.*—Very strong.

*Stipules.*—Large, adnate to petiole, foliar, grow to 9 cm long and 11 cm wide, irregularly incised, pubescent on both sides; leaves and stipules colored topside RHS N137A with veins RHS 144B, bottom side colored RHS 147B with the same for veins.

*Rachis size.*—Grows to 2 cm wide and 11 cm long.

*Rachis texture.*—Pubescent.

*Rachis color.*—RHS 144B where shaded and RHS N77A where exposed to sun.

*Pedicel.*—Variable in length, 5.5 cm to 16 cm long and 2 mm to 3.5 mm wide.

*Pedicel color.*—RHS 144B where shaded and RHS N77A where exposed to sun.

*Flower bud size.*—13 mm long and 0.5 cm wide.

*Flower bud shape.*—Conic, nodding.

*Flower bud texture.*—Pubescent.

*Flower bud color.*—Between RHS 187A to RHS 187B.

*Corolla description.*—Usually 10-21 petals. Broadly obovate in shape, grows to 2.5 cm deep and 4.8 cm wide, tip notched to sometimes obtuse, base truncate, glabrous on both sides.

*Petal color.*—Highly variable. Young petals are colored RHS 14B tinted with veins RHS N25B. Outer margin colored completely to not colored RHS 33B. At base closest to RHS 2B, bottom side colored RHS N34C with variations of RHS 1B; older flowers top side RHS 13A with some veins close to RHS 26A. Margins are RHS 33A fading down petal to RHS 32B with base RHS 13A. Underside is RHS 8B at base to RHS 13C with veins and margins to RHS 20A.

*Calyx description.*—5 main sepal lobes alternating with 5 smaller lobes, stellate, 28 mm wide overall, colored RHS 147B inside, outside RHS 187A.

*Calyx texture.*—Pubescent on outside and glabrous inside.

*Calyx lobes.*—Triangular, margins entire, tips acuminate and reflexed, main lobes 9 mm long and 6 mm wide, smaller lobes 4.5 mm long and 1 mm wide.

*Pistil.*—About 125 hair-like pistils forming a clump 1.5 cm in diameter, colored RHS 152D and RHS 178D near stigma, covered with white hairs.

*Stigma number.*—1.

*Style.*—7 mm long, <1 mm wide, hooked.

*Ovary.*—2 mm long and <2 mm wide.

*Ovary color.*—RHS 144D tinted RHS N43A.

*Stamen number.*—About 120.

*Stamen size.*—4.5 mm long, filaments 4 mm long.

*Stamen color.*—RHS 153D.

*Anther description.*—0.5 mm long, colored RHS 17B.

*Pollen color.*—RHS 8B.

*Date of bloom.*—April to May with rebloom through November.

*Lastingness of individual blooms.*—Each flower lasts approximately one week in summer and up to two weeks in cool weather.

*Fragrance.*—None. No fruit or seeds were present at time of observation.

Disease/pest resistance: Appears typical to the genus *Geum.*

I claim:

1. A new and distinct *Geum coccineum* plant named 'Fiesta' substantially as illustrated and described herein.

* * * * *